US00PP10796P

United States Patent [19]

Egger et al.

[11] Patent Number: Plant 10,796

[45] Date of Patent: Feb. 16, 1999

[54] ASIATIC HYBRID LILY PLANT NAMED 'CEB LATTE'

[75] Inventors: Donald L. Egger, Wilsonville; Teresa Pankiewicz-Leap, Portland, both of Oreg.

[73] Assignee: Cebeco Lilies, Inc., Aurora, Oreg.

[21] Appl. No.: 918,034

[22] Filed: Aug. 25, 1997

[51] Int. Cl.[6] ..... A01H 5/00

[52] U.S. Cl. ..... Plt./87.4

[58] Field of Search ..... Plt./87.4

*Primary Examiner*—Howard J. Locker

*Attorney, Agent, or Firm*—Klarquist Sparkman Campbell Leigh & Whinston, LLP

[57] ABSTRACT

A new and distinct Asiatic Lily Hybrid having upright facing, double flowers of red and light orange to cream, on vigorous, strong stems suitable for the garden or for greenhouse forcing for small bouquets.

2 Drawing Sheets

BACKGROUND OF THE INVENTION

The present invention relates to a new and distinct cultivar of Lily hybrid referred to commercially as an upright Asiatic hybrid lily and given the cultivar name 'Ceb Latte'. This invention was discovered in a plot of seedlings that were of mixed parentage that were bred for pollen free stock.

This invention has not been observed under all possible environmental conditions. The phenotype may vary significantly with variations in environment such as temperature, light intensity and day length, without, however, any variation in genotype.

The following traits have been repeatedly observed and are determined to be the basic characteristics of this invention which in combination distiguish this lily as new and distinct cultivar: 1) double flowers of medium size; 2) flowers of red and light orange to cream; 3) strong stems suitable for the garden or for forcing for small bouquets; 4) blooms mid-season; and 5) good vigor. Bulbs of this plant may be precooled and forced out of season for uniform cut flower production. In addition, this new lily shows good disease resistance.

Of the many cultivars known to the inventor, the inventor is not aware of any other double Asiatic lily commercially available with the unique color and striking pattern of this invention.

Asexual reproduction of this new variety has been accomplished at Cebeco Lilies, Inc., Aurora, Oreg., by scaling and tissue culture. The resulting plants have shown that the above-mentioned unique features are stable and reproduce true to type in each successive propagation.

Figure 1:
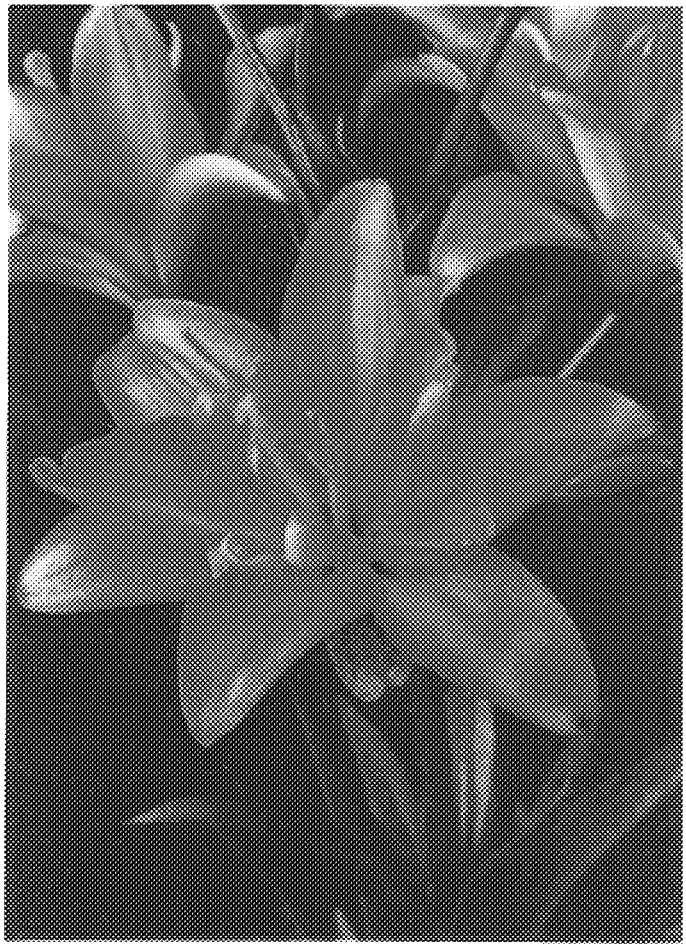
FIG. 1 is a close-up photograph which illustrates in greater detail a single flower of the new plant.
Figure 2:
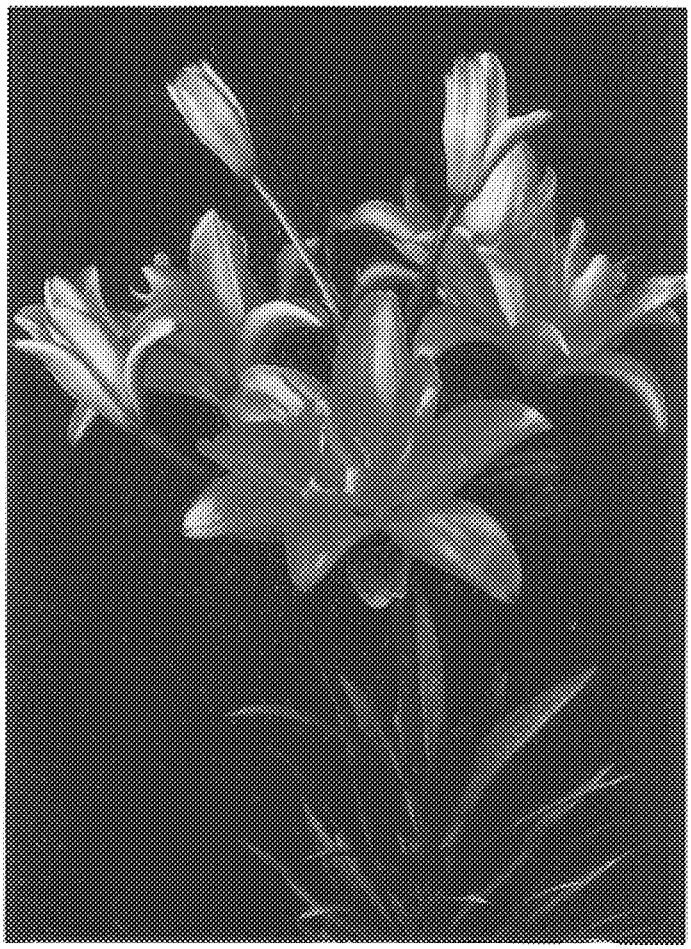
FIG. 2 is a photograph showing the 'Ceb Latte' lily.

The photographs of the drawing were taken in June 1995 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. fields in Aurora, Oreg. in June 1995. Color references are made to The Royal Horticultural Society Colour Chart, except where the context indicates a term having its ordinary dictionary meaning.

The Plant

Origin: Seedling.

Parentage:

*Seed parent.*—Unknown.

*Pollen parent.*—Unknown.

Commercial classification: Hybrid Asiatic lily.

Classification: Division I-A, Upright Asiatic Hybrid Lily, according to the Horticultural Classification of Lilies by The Royal Horticultural Society of London.

Form: Single erect stem bearing terminal cluster of flowers.

Height: About 57 cm. from the top of the soil to the top of the flowers from bulbs of 12–14 cm. in circumference.

Stem color: Yellow green 144A mottled with maroon spots 187A.

Growth habit: Vigorous, upright and rigid.

Foliage:

*Arrangement.*—Spiral.

*Leaf size.*—Variable, about 83 mm. long and 13 mm. wide.

*Leaf shape.*—Lanceolate.

*Texture.*—Leathery.

*Aspect.*—Glossy.

*Color.*—Medium green on both sides. Closest to Yellow Green Group 147A.

Bulbs:

*Size.*—Variable, ranging to about 12 to 16 cm. in circumference as used commercially.

*Color.*—White.

The Bud

Size: Small, to about 44 mm. long and 18 mm. wide just prior to opening.

Shape: Ovoid with an obtuse tip.

Rate of opening: The mature bud opens slowly in response to light.

Color: Yellow green prior to opening. Yellow Green Group 144B at the midrib and lightening at tepal edges, showing a red edge (33A) when partially open.

The Flower

Blooming habit: Annually, once and mid-season.

Days to bloom: Flowers approximately 78 days after spring greenhouse planting under typical commercial flower forcing conditions of 15 degrees Celsius night time temperatures.

Inflorescence size: About 14 cm. high and 19 cm. wide when there are three flowers present.

Flower size: Medium.

*Diameter.*—About 11 cm.

*Depth.*—About 5.5 cm.

Borne: In an umbel-like raceme of 3 to 5 flowers from bulbs 12 to 14 cm. in circumference.

Shape: Bowl shaped. Outer tepels reflex slightly at the tips.

Tepalage:

*Number.*—Twelve. Six outer tepals and six inner. The six inner tepals are in two series of three, like the six outer tepals. The inner tepals of each series are in an alternate arrangement. The tepals of the first inner series of tepals are larger, and the tepals of the second inner series of tepals are smaller, with sterile stamens at the tip, giving them a notched appearance.

*Arrangement.*—Imbricate.

*Shape.*—Ovate.

*Texture.*—Waxy.

*Aspect.*—Satiny.

*Size.*—Length: Outer six petals — about 60 mm. Inner tepals, first series — about 67 mm. Inner tepals, second series — about 52 to 58 mm. and irregular. Width: Outer tepals — about 28 to 32 mm. Inner tepals, first series — about 31 mm. Inner tepals, second series — about 25 to 28 mm.

*Nectary.*—About 13 mm. long; yellow green; smooth and fairly flat; channels together.

*Projections.*—None.

*Spots.*—None.

*Blush.*—Light orange (28C) and/or cream (27A).

*Color.*—Two or three toned; red, light orange and cream.

Topside: Tepals having varying amounts of dark red (closest to 53A) at the edges and tips and sometimes halfway down midrib from the tip with the midrib and blush with varying amounts of cream (27A) to light orange (28C). Bottomside: Three toned. The edges are red 53A, alongside the midrib is cream (27A), and the midrib is yellow green (144A).

*Discoloration.*—Darkens with age.

*Fragrance.*—None.

Pedicel:

*Length.*—About 6 to 10 cm.

*Color.*—Yellow green (144A) overlaid with maroon spots, Greyed-Purple Group 187A. The spots are heaviest where the sun reaches the pedicel.

*Orientation.*—Ascending upwardly 20 degrees to 60 degrees from the horizontal.

The Reproductive Organs

Stamens:

*Number.*—Three sterile and six stamenoid tepals, the three innermost terminating in sterile stamens.

*Anthers.*—None.

*Filaments.*—Curling at the tips where anthers would be. Length: About 43 mm. Color: Greyed red 181A on the top half to white at the bottom.

*Pollen.*—None.

Pistil:

*Number.*—One.

*Style.*—Length: About 37 mm. Color: Light orange 25D.

*Stigma.*—Color: Orange red 34D.

The Fruit

Fertility: Fertile.

Shape: Ovoid.

Color at maturity: Soft brown.

We claim:

1. A new and distinct cultivar of Asiatic hybrid lily plant substantially as herein shown and described.

* * * * *